United States Patent [19]

Cook et al.

[11] Patent Number: 4,503,235

[45] Date of Patent: Mar. 5, 1985

[54] PROCESS FOR PRODUCING 4-CARBAMOYL-1H-IMIDAZOLIUM-5-OLATE

[75] Inventors: Phillip D. Cook; Dennis J. McNamara, both of Ann Arbor, Mich.

[73] Assignee: Warner-Lambert Company, Morris Plains, N.J.

[21] Appl. No.: 474,410

[22] Filed: Mar. 11, 1983

[51] Int. Cl.³ ............................................ C07D 233/70
[52] U.S. Cl. .................................................... 548/301
[58] Field of Search .......................................... 548/301

[56] References Cited

U.S. PATENT DOCUMENTS 4,218,457 8/1980 Atsumi et al. ...................... 548/301

OTHER PUBLICATIONS

Schipper and Day, J. Am. Chem. Soc., 74, pp. 350–353, 1952.

*Primary Examiner*—Henry R. Jiles
*Assistant Examiner*—Kurt G. Briscoe
*Attorney, Agent, or Firm*—Jerry F. Janssen

[57] ABSTRACT

A process is provided for producing 4-carbamoyl-1H-imidazolium-5-olate (I)

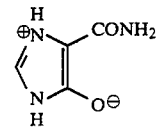

by reacting aminomalonamide $H_2N-CH(CONH_2)_2$ and formamidine $CH(=NH)NH_2$ compound in a liquid medium comprising alcohol under conditions such that the product I can be obtained in a solid form that is directly recoverable from the medium, free of aminomalonamide and recrystallizable.

5 Claims, No Drawings

PROCESS FOR PRODUCING 4-CARBAMOYL-1H-IMIDAZOLIUM-5-OLATE

DESCRIPTION

1. Technical Field

The invention relates to a novel process for producing 4-carbamoyl-1H-imidazolium-5-olate (also referred to as bredinin aglycone or 5-hydroxyimidazole-4-carboxamide) which is a substance that has useful pharmacological properties such as antitumor, antirheumatic and antinephritic properties. The product of the process also is useful as a starting material for the production of antibiotic compounds and other compounds.

2. Background of the Invention

Schipper and Day first synthesized 4-carbamoyl-1H-imidazolium-5-olate by reacting aminomalonamide with triethyl orthoformate at 145 degrees for two hours; Studies in Imidazoles. II. Imidazo[b]pyrazines, E. Schipper and A. R. Day, J. Am. Chem. Soc., 74, 350-353 (353), 1952. The method, however, is inefficient in that product obtained from this procedure typically is contaminated with starting material aminomalonamide. Repeated recrystallizations gradually reduce this contaminant, but lowering of the yield of pure material takes place as a result. A similar method in which aminomalonamide is refluxed with acetic acid in triethyl orthoformate for 0.5 hours also is inefficient, and the product obtained is contaminated with aminomalonamide as in the procedure of Schipper and Day; 5-Hydroxyimidazole-4-carboxamide; T. Atsume, Y. Takebayashi, J. Katsube, and H. Yamamoto; Sumitomo Chemical Co., Ltd., Japan, Kokai; Japanese Pat. No. 76 88,965, Jan. 29, 1975.

SUMMARY OF THE INVENTION

The present invention relates to a process for producing 4-carbamoyl-1H-imidazolium-5-olate (I)

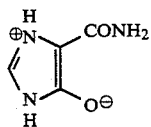

which comprises reacting substantially equimolar amounts of aminomalonamide $H_2N-CH(CONH_2)_2$ and formamidine $CH(=NH)NH_2$ compound in a liquid medium comprising alcohol under conditions such that the product I can be obtained in a solid form that is directly recoverable from the medium, free of aminomalonamide and recrystallizable.

Use of formamidine in place of triethyl orthoformate or ethyl formimidate and acid catalysts provides a simple, high yield process to pure 4-carbamoyl-1H-imidazolium-5-olate. Surprisingly, the condensation is specific for the formic acid amidine; substituted formamidines such as acetamidine and benzamidine hydrochlorides do not yield 2-substituted imidazoles. This procedure also fails to yield 2-heteroatom substituted imidazoles by use of substituted amidines such as guanidine or methylthiopseudourea acid salts. The condensation is specific for the formic acid amidine, either as the free base or as the salt such as the hydrochloride salt or acetic acid salt, sometimes referred to hereinafter as formamidine compound. An acid salt of formamidine and an equivalent amount of base such as triethylamine, sodium methoxide, or potassium carbonate also provides 4-carbamoyl-1H-imidazolium-5-olate, according to the invention. Advantageously, the process uses low boiling alcohol solvent (e.g., ethanol or methanol) rather than high boiling solvent such as triethyl orthoformate, the latter also serving in the prior art as the reactant. Unlike other processes, where aminomalonamide starting material is the principal contaminant and is difficult to remove, the present reaction goes to completion. Further, in the present process the desired product precipitates out directly. The precipitated material is relatively pure and by only one recrystallization is rendered analytically pure, whereas repeated recrystallization or ion exchange chromatography is required in the prior art. Finally, the process provides a high yield of the mentioned pure 4-carbamoyl-1H-imidazolium-5-olate.

The reaction conditions are subject to some variation. For best results one employs aminomalonamide in the ratio of approximately one mole to one mole of formamidine compound. In other words, a substantial excess of aminomalonamide is avoided. The reaction is carried out in a compatible solvent, preferably a relatively low boiling solvent comprising alcohol, preferably methanol or ethanol, and more preferably ethanol alone. For best results, one uses formamidine acetate and one further uses about 2 to about 4 liters of ethanol for each mole of formamidine acetate. The reaction conveniently is carried out by maintaining the reactants as a suspension in the solvent and at the reflux temperature of the reaction medium. The reaction is substantially complete within short periods, e.g., within about one hour, and thereafter the resulting suspension of product can be stirred at room temperature overnight to ensure completion of the reaction. The product is obtained as an off-white suspension that can conveniently be recovered as a solid by filtration. Recrystallization is achieved using water as a solvent.

The invention and the best mode of practicing the same are illustrated by the following example of a preferred embodiment.

EXAMPLE

4-Carbomoyl-1H-imidazole-5-olate.

A suspension of 105.5 g of aminomalonamide and 112.5 g of formamidine acetate of 4.0 liters of ethanol was heated under reflux for one hour. The resulting off-white suspension was stirred at room temperature overnight and filtered. Recrystallization of the solid from approximately 2 liters of water, following by drying under reduced pressure at 100 degrees gave 93 g (78 percent) of the product as a dark blue-grey solid, mp 255 degrees. PMR spectroscopy of the product in deuterated dimethylsulfoxide indicated an absence of aminomalonamide. TLC (SiO$_2$ CH$_3$CN:0.2 M NH$_4$Cl, 3:1) revealed an homogeneous product with an R$_f$ of 0.34.

Anal calcd. for C$_4$H$_5$N$_3$O$_2$.0.35 H$_2$O: C, 36.01; H, 4.31; N, 31.50; H$_2$0, 4.72; Found: C, 36.06; H, 4.13; N, 31.53; H$_2$O, 5.08.

Having thus described our invention, what we claim and desire by Letters Patent to secure are the following:

1. A process for producing 4-carbamoyl-1H-imidazolium-5-olate, which comprises reacting substantially equimolar amounts of aminomalonamide and formamidine compound in a liquid medium comprising a low-boiling alcohol under reflux conditions to form the product in a solid form that is directly recoverable from the medium by filtration and is free of aminomalonamide.

2. A process according to claim 1 where the liquid medium is ethanol.

3. A process according to claim 2 where the formamidine compound is formamidine acetate.

4. A process according to claim 3 where about 2 to about 4 liters of ethanol are employed for each mole of formamidine acetate.

5. A process according to claim 1 where the product is recovered in solid form from the reaction medium and recrystallized from water.